US008821702B2

(12) United States Patent
Sjong

(10) Patent No.: US 8,821,702 B2
(45) Date of Patent: Sep. 2, 2014

(54) DEVICES AND METHODS FOR ELECTROOSMOTIC TRANSPORT OF NON-POLAR SOLVENTS

(75) Inventor: Angele Sjong, Louisville, CO (US)

(73) Assignee: Empire Technology Development LLC, Wilmington, DE (US)

( * ) Notice: Subject to any disclaimer, the term of this patent is extended or adjusted under 35 U.S.C. 154(b) by 127 days.

(21) Appl. No.: 13/382,498

(22) PCT Filed: Aug. 27, 2010

(86) PCT No.: PCT/US2010/046918
§ 371 (c)(1),
(2), (4) Date: Jan. 5, 2012

(87) PCT Pub. No.: WO2012/026942
PCT Pub. Date: Mar. 1, 2012

(65) Prior Publication Data
US 2012/0186977 A1    Jul. 26, 2012

(51) Int. Cl.
*G01N 27/447*   (2006.01)
*C25B 15/00*    (2006.01)
*B01L 3/00*     (2006.01)

(52) U.S. Cl.
CPC ........... *B01L 3/50273* (2013.01); *G01N 27/447* (2013.01); *B01L 3/502707* (2013.01); *B01L 3/502746* (2013.01); *B01L 3/502784* (2013.01); *B01L 2300/165* (2013.01); *B01L 2400/0418* (2013.01); *B01L 2400/0448* (2013.01); *B01L 2400/0487* (2013.01)
USPC .......................................... 204/451; 204/601

(58) Field of Classification Search
CPC .............. G01N 27/447; B01L 13/5027; B01L 13/50273; B81C 1/00015–1/00341; B81C 2201/0174–2201/0197

USPC .................................................. 204/451, 601
See application file for complete search history.

(56) References Cited

U.S. PATENT DOCUMENTS

| 6,878,254 B2* | 4/2005 | Yeung et al. ................ 204/451 |
| 7,081,189 B2 | 7/2006 | Squires et al. |
| 7,204,922 B1 | 4/2007 | Kahl et al. |
| 2007/0286773 A1 | 12/2007 | Schlautmann et al. |
| 2011/0091864 A1 | 4/2011 | Karlsson et al. |

FOREIGN PATENT DOCUMENTS

| GB | 2 462 364 | 2/2010 |
| JP | 2008-525797 | 7/2008 |
| WO | WO-02/052045 | 7/2002 |

OTHER PUBLICATIONS

Ding et al. (Electrophoresis 2010, 31, 1983-1990).*
Hautala et al. (Anal. Bioanal. Chem., 2004, 378, 1769-1776).*
"Agilent capillary electrophoresis system".*
"Sigma Product Specification".*
"Corning Fused Silica".*
Diress et al. (Canadian Journal of Chemistry, 2007, http://www.highbeam.com/doc/1G1-167778893.html/print, accessed Apr. 24, 2014).*
Pei et al. (J. Chromatography A, 1267, 2012, 80-88).*

(Continued)

*Primary Examiner* — Luan Van
*Assistant Examiner* — Steven Rosenwald
(74) *Attorney, Agent, or Firm* — Foley & Lardner LLP

(57) ABSTRACT

A microdevice for supporting a flowing nonpolar fluid is disclosed. The microdevice includes a substrate that is at least partially coated by one or more amphiphilic layers. Methods for using the device in biological and chemical assays are also disclosed.

15 Claims, 4 Drawing Sheets

(56) References Cited

OTHER PUBLICATIONS

Aghdaei, S. et al., "Formation of artificial lipid bilayers using droplet dielectrophoresis," Lab on a Chip, 2008, published on Web Aug. 13, 2008, vol. 8, pp. 1617-1620, supp. pp. 1-7.
Castellana, E.T. et al., "Solid supported lipid bilayers: From biophysical studies to sensor design," Surface Science Reports, 2006, vol. 61, pp. 429-444.
Electrokinetic, "Technology," printed on Aug. 29, 2011, retrieved from the internet at http://www.electrokinetic.co.uk/technology/, 1 page.
Gruen, D.W.R. et al., "The adsorption of nonpolar molecules into lipid bilayer membranes," Biophys. J., Apr. 1980, vol. 30, pp. 129-136.
Helm, C.A. et al., "Role of Hydrophobic Forces in Bilayer Adhesion and Fusion," Biochemistry, 1992, vol. 31, No. 6, pp. 1794-1805.
Ichikawa, T. et al., "Immobilizing Single Lipid and Channel Molecules in Artificial Lipid Bilayers with Annexin A5," Langmuir, 2006, published on web Jun. 1, 2006, vol. 22, No. 14, pp. 6302-6307.
Ide, T. et al., "A novel method for artificial lipid-bilayer formation," Biosensors and Bioelectronics, 2005, vol. 21, pp. 672-677.
International Search Report and Written Opinion for PCT/US2010/046918 mailed Oct. 8, 2010.
Israelachvili, J.N. et al., "Measurement of the hydrophobic interaction between two hydrophobic surfaces in aqueous electrolyte solutions," Journal of Colloid and Interface Science, Apr. 1984, vol. 98, No. 2, pp. 500-514.
Morgan, H. et al., "Artificial lipid bilayers in a microfabricated system," In: 8th International Conference on Miniaturized for Chemistry and Life Science, Sep. 26-30, 2004, Malmo, Sweden, pp. 330-332.
Peterman, M.C. et al., "Ion Channels and Lipid Bilayer Membranes Under High Potentials Using Microfabricated Apertures," Biomedical Microdevices, 2002, vol. 4, No. 3, pp. 231-236.
Pope, J.M. et al., "The interaction of n-alkanes and n-alcohols with lipid bilayer membranes: a $^2$H-NMR study," Biochimica et Biophysica Acta, 1986, vol. 858, pp. 243-253.
Richter, R.P. et al., "Formation of Solid-Supported Lipid Bilayers: An Integrated View," Langmuir, 2006, vol. 22, No. 8, pp. 3497-3505.
Sandison, M.E. et al., "Air-Exposure Technique for the Formation of Artificial Lipid Bilayers in Microsystems," Langmuir, 2007, vol. 23, No. 15, pp. 8277-8284.
Sandison, M.E. et al., "Micromachined glass apertures for artificial lipid bilayer formation in a microfluidic system," J. Micromech. Microeng., 2007, vol. 17, pp. S189-S196.
Smith, R.A. et al., "The Solubility of Anesthetic Gases in Lipid Bilayers," Biochimica et Biophysica Acta, 1981, vol. 645, pp. 327-338.
Starr, T.E. et al., "Formation and Characterization of Planar Phospholipid Bilayers Supported on $TiO_2$ and $SrTiO_3$ Single Crystals," Langmuir, 2000, vol. 16, No. 26, pp. 10301-10308.
Tandon, V. et al., "Zeta potential and electroosmotic mobility in microfluidic devices fabricated from hydrophobic polymers: 1. The origins of charge," Electrophoresis, 2008, vol. 29, pp. 1092-1101.
White, S.H. et al., "Location of hexane in lipid bilayers determined by neutron diffraction," Nature, Mar. 12, 1981, vol. 290, pp. 161-163.
Wikipedia, "Electro-osmosis," printed on Aug. 29, 2011, retrieved from the internet at http://en.wikipedia.org/wiki/Electroosmotic_flow, 4 pages.
Wikipedia, "Lipid bilayer," printed on Aug. 29, 2011, retrieved from the internet at http://en.wikipedia.org/wiki/Lipid_bilayer, 18 pages.
Wikipedia, "Liquid crystal," printed on Aug. 29, 2011, retrieved from the internet at http://en.wikipedia.org/wiki/Liquid_crystal, 14 pages.
Wong, J.Y. et al., "Polymer-cushioned bilayers. I. A structural study of various preparation methods using neutron reflectometry," Biophysical Journal, Sep. 1999, vol. 77, pp. 1445-1457.
Yang, J., "Viscoelastic wormlike micelles and their applications," Current Opinion in Colloid & Interface Science, 2002, vol. 7, pp. 276-281.

\* cited by examiner

DEVICES AND METHODS FOR ELECTROOSMOTIC TRANSPORT OF NON-POLAR SOLVENTS

CROSS-REFERENCE TO RELATED APPLICATIONS

The present application is a U.S. national stage application of International Application No. PCT/US2010/046918, filed on Aug. 27, 2010, the entire contents of which is incorporated herein by reference in its entirety.

TECHNICAL FIELD

The present technology relates generally to the field of microfluidics. In particular, the present technology relates to microfluidic devices and methods of making and using microfluidic devices.

BACKGROUND

The following description is provided to assist the understanding of the reader. None of the information provided or references cited is admitted to be prior art.

The ability to transport fluids in micron-sized channels is important for many emerging technologies, such as in vivo drug delivery devices, micro-electro-mechanical systems (MEMS), and micro-total-analysis systems (µTAS). Common fluids used in microfluidic devices include whole blood samples, bacterial cell suspensions, protein or antibody solutions and various buffers. Microfluidic devices can be used to obtain a variety of measurements including molecular diffusion coefficients, fluid viscosity, pH, chemical binding coefficients and enzyme reaction kinetics. Other applications for microfluidic devices include capillary electrophoresis, isoelectric focusing, immunoassays, flow cytometry, sample injection of proteins for analysis via mass spectrometry, PCR amplification, DNA analysis, cell manipulation, cell separation, cell patterning and chemical gradient formation. Many of these applications have utility for clinical diagnostics.

The use of microfluidic devices to conduct pharmaceutical research and create clinically useful technologies has a number of significant advantages. First, because the volume of fluids within these channels is usually several microliters or nanoliters, the amount of reagents and analytes used is quite small. This is especially useful for expensive reagents. The fabrications techniques used to construct microfluidic devices are relatively inexpensive and are very amenable both to highly elaborate, multiplexed devices and also to mass production. In a manner similar to that for microelectronics, microfluidic technologies enable the fabrication of highly integrated devices for performing several different functions on the same substrate chip.

There are two common methods by which fluid actuation through microchannels can be achieved. In pressure driven flow, the fluid is pumped through the device via positive displacement pumps, such as syringe pumps. Another common technique for pumping fluids is that of electroosmotic pumping. If the walls of a microchannel have an electric charge, as most surfaces do, an electric double layer of counter ions will form at the walls. When an electric field is applied across the channel, the ions in the double layer move towards the electrode of opposite polarity. This creates motion of the fluid near the walls and transfers via viscous forces into convective motion of the bulk fluid. If the channel is open at the electrodes, the velocity profile is uniform across the entire width of the channel. Devices utilizing the electroosmotic effect are particularly applicable in microfluidics where the manipulation of small amounts of electrolyte solution is required to perform chemical or biochemical reactions.

SUMMARY

In one aspect, the present disclosure provides a microfluidic device comprising: at least one fluid channel and at least one pair of electrodes configured to provide an electric field in the at least one channel, wherein the interior of the at least one channel is at least partially coated by one or more amphiphilic layers. In one embodiment, the one or more amphiphilic layers form a hydrophobic space in the interior of the channel. In one embodiment, the at least one channel has a diameter between about 0.1 µm and about 500 µm.

In one embodiment, the one or more amphiphilic layers include one or more lipid layers. In one embodiment, the one or more lipid layers covering the one or more substrates form a bilayer. In one embodiment, the one or more lipid layers form a worm-like micelle. In one embodiment, the one or more lipid layers comprises at least one of a phospholipid, sphingolipid, or glycolipid. In illustrative embodiments, the phospholipid is selected from the group consisting of: phosphatidylcholine, phosphatidylserine, phosphatidylethanolamine, and phosphatidylglycerol. In one embodiment, the one or more lipid layers has a fatty acyl chain length which defines the volume of an interior hydrophobic region of the channel. In an illustrative embodiment, the fatty acyl chain length is from 2 to 30. In one embodiment, the interior of the at least one channel is totally covered by the one or more amphiphilic layers.

In one embodiment, the electric field produces an electroosmotic flow in the at least one channel. In one embodiment, each electrode of the at least one pair of electrodes is located on a laterally opposite wall of the at least one channel directly across or offset from the other electrode of the electrode pair. In one embodiment, negatively charged electrodes extend on one side of the channel and positively charged electrodes extend on the opposite side of the channel. In one embodiment, the electric field is a DC electric field. In one embodiment, the electric field is an AC electric field.

In one embodiment, the device further comprises a voltage controller in electrical contact with the at least one pair of electrodes. In one embodiment, the device further comprises a computer operably linked to the voltage controller.

In one embodiment, the boundaries of the at least one channel are defined by one or more materials selected from the group consisting of: glass, quartz, platinum, stainless steel, copper, aluminum, nickel, gold, titanium, ceramic, diamond, silicon, silicon nitride, silicone, high-density polyethylene, polyethylene terephthalate, polydimethylsiloxane, polymethyl-methacrylate, polystyrene, cellulose acetate, polyimide, and polycarbonate. In one embodiment, the device further comprises one or more input ports and one or more output ports in fluid communication with the at least one channel.

In one aspect, the present disclosure provides a method of circulating or conducting a fluid, the method comprising: adding a fluid to a device having at least one fluid channel and at least one pair of electrodes; providing an electric field in the at least one channel, wherein the interior of the at least one channel is at least partially covered by one or more amphiphilic layers; and applying an electric field to the at least one fluid channel to generate an electro-osmotic flow. In one embodiment, the fluid is a non-polar solvent. In exemplary embodiments, the non-polar solvent is selected from the group consisting of: propane, butane, pentane, hexane, heptane, octane, nonane, decane, cyclopentane, cyclohexane, benzene, toluene, xylene, squalene, diethyl ether, diisopropylether, ethylacetate, 2-butanone, carbon tetrachloride, chloroform, methylene chloride, tetrachloroethane, trichlorethane, dichloroethane, and ethyl acetate.

In one aspect, the present disclosure provides a method of carrying out an organic reaction in a non-polar solvent, the method comprising: adding one or more reactants and one or more non-polar solvents to a device having at least one fluid channel and at least one pair of electrodes providing an electric field in the at least one channel, wherein the interior of the at least one channel is at least partially covered by one or more amphiphilic layers; and applying an electric field to the at least one fluid channel to generate an electro-osmotic flow in which to mix the one or more reactants.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 3a is an illustrative embodiment of the Langmuir-Blodgett technique of pulling a hydrophilic substrate through a lipid monolayer and sequentially pushing it horizontally through another lipid monolayer. FIG. 3b is an illustrative embodiment of vesicles in solution that adsorb and spontaneously fuse to the surface to form a solid supported lipid bilayer. FIG. 3c is an illustrative embodiment showing a combination of the Langmuir-Blodgett and vesicle fusion processes.

DETAILED DESCRIPTION

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented here.

The present technology is described herein using, unless otherwise stated, the singular forms "a," "an," and "the" to include plural reference. Thus, for example, a reference to "a channel" includes a plurality of channels.

Transport of solvents in microfluidic devices may be facilitated by electroosmotic flow (EOF). EOF is the motion of liquid induced by an applied potential across a capillary tube or microchannel. When a voltage is applied across microchannel, ion migration takes place. Positive ions (cations) are attracted to the cathode and repelled from the anode and negative ions (anions) are forced in the opposite direction. As the cations migrate along the solid boundary layer they drag with them their water of hydration and exert a viscous drag upon the fluid around them. EOF provides a very efficient way to generate fluid flows in microfluidic devices. Electroosmotic pumps can generate flow rates as large as a few milliliters per minute, and pressures as large as hundreds of atmospheres. In one aspect, the present disclosure provides a microfluidic device capable of transport of nonpolar solvents using EOF. The majority of organic chemical reactions take place in non-polar solvents, or a combination of non-polar and polar. Therefore, transport of nonpolar solvents in microreactors using EOF techniques can be useful in a variety of contexts such as, but not limited to, the performance of high throughput screening assays in drug discovery, immunoassays, diagnostics, genetic analysis, and the like.

In some embodiments, amphiphilic molecules (e.g., arranged in one or more lipid layers) are used to transport nonpolar solvent reaction mixtures through microchannels by EOF. The hydrophilic, charged headgroups of the amphiphilic molecules are associated with counter ions that interact with the microchannel wall. The hydrophobic tails point inward to create an interior space (or lumen) inside the channel which encloses the non-polar solvent. When a charge is applied to the channel, the movement of the counter ions causes the amphiphilic molecules and solvent to move through the channel by EOF. The volume of the nonpolar area is controlled by varying the chain length or extent of double bonds in the hydrocarbon chain.

Figure 1:
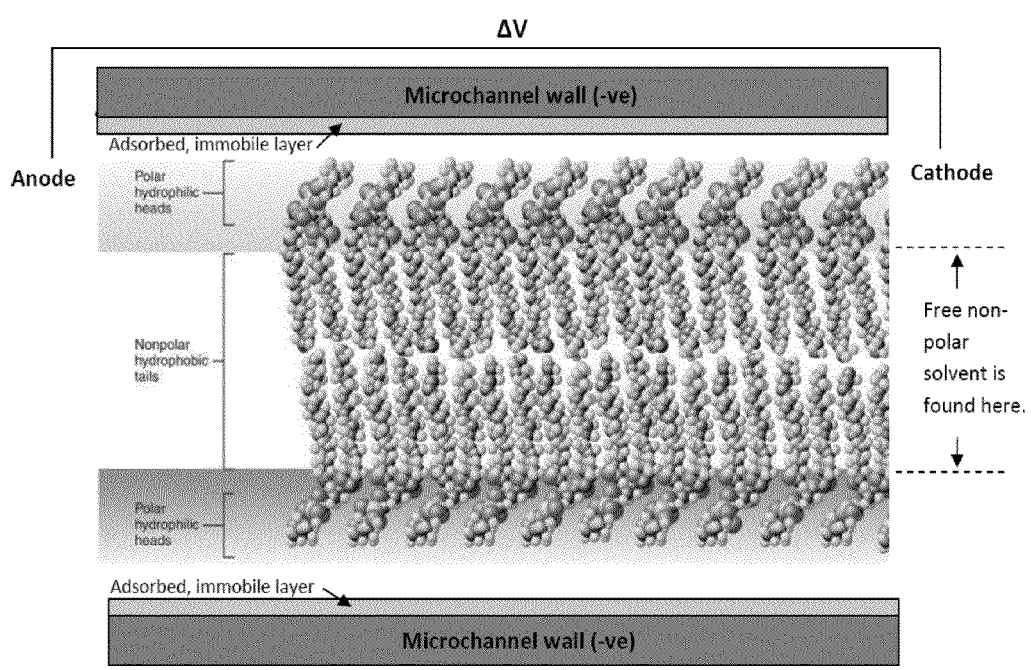
FIG. 1 is schematic illustration of a cross-section of a microfluidic channel containing amphiphilic layers for the transport of nonpolar solvents.

FIG. 1 schematically illustrates one embodiment wherein a microfluidic device contains a channel. In this embodiment, the device is constructed to form a four-walled channel, but the device may also form a three-walled channel, tube, or other shapes. Because the device is shown in cross section, only two sides are depicted in the diagram. Although two lipid layers are shown within the channel cross-section, the lipid layer forms a tube within the intact channel that substantially conforms to the channel walls by the interaction of polar head groups with a charged surface on the channel walls. The interior of the tube formed by the lipid layer contains the non-polar solvent. The device includes a pair of electrodes to generate a potential at either end of the channel. A cathode is positioned on one end of the channel and an anode positioned on the opposite end such that when a voltage is applied to the electrodes, EOF within the channel is produced, moving the lipid tube and the non-polar solvent along with it.

In brief, EOF occurs when a fluid is placed into a channel that has a surface bearing (or coated with) charged functional groups that are able to ionize. In an illustrative embodiment, the channel may be etched glass channels or glass microcapillaries having ionizable hydroxyl groups. The nature of the charged functional groups can vary depending upon the material forming the channel wall and the treatments to which that mateiral is subjected, as described in greater detail below. In the case of hydroxyl functional groups, ionization at neutral pH, for example, results in the release of protons from the surface into the fluid, resulting in a localization of cationic species within the fluid near the surface. That results in the creation of a positively charged sheath surrounding the bulk fluid in the channel. Application of a voltage gradient from one end to the other of the channel will cause the cation sheath to move in the direction of the voltage drop, i.e., toward the negative electrode, moving the bulk fluid and lipid molecules along with it.

The term "channel" or "chamber" is used in a broad sense. Thus, it is not intended to be restricted to elongated configurations where the transverse or longitudinal dimension greatly exceeds the diameter or cross-sectional dimension. Rather, such terms are meant to include cavities or tunnels of any desired shape or configuration, such as three- or four-walled channels or tubes, through which liquids may be directed. Such a fluid cavity may, for example, include a flow-through cell where fluid is to be continually passed or, alternatively, a chamber for holding a specified, discrete amount of fluid for a specified amount of time. "Channels" and "chambers" may be filled or may contain internal structures comprising, for example, valves, filters, and similar or equivalent components and materials.

The term "microfluidic device" as used herein is to be understood, without any restriction thereto, to refer to structures or devices through which fluid(s) are capable of being passed or directed, wherein one or more of the dimensions is less than 500 microns. Additionally, such devices can be constructed using any of the materials described herein, as well as combinations of such materials and similar or equivalent materials.

In some embodiments, the presently disclosed devices and methods may be used for flowing a material and/or mixing two or more materials in a microfluidic device. In some embodiments, the devices are used for conducting a chemical reaction. In some embodiments, the devices are used for a method of screening a sample for a characteristic. In some embodiments, the devices are used for a method of dispensing a material. In some embodiments, the devices are used for a method of separating a material.

Devices and Substrates

The disclosed devices include a substrate, which typically functions to define the boundaries of the microfluidic channels. Any suitable material may be used to form the substrate defining the fluid channels in the microdevice. The materials used may be organic or inorganic, and may be transparent, translucent, or non-transparent. Suitable materials for the substrate can include, and are not limited to, silicon (single crystal or polycrystalline), coatings on silicon (e.g. silicon nitride), silicone, glass, quartz, platinum, stainless steel, copper, aluminum, nickel, gold, titanium, ceramics, diamond, and/or plastics. Additional substrates can include, and are not limited to, polyalkylene polymers and copolymers, fluorocarbon polymers and copolymers, polyester polymers and copolymers, polyether polymers and copolymers, silicone polymers and copolymers, and polyurethane polymers and copolymers. Other polymers that can be used include, and are not limited to, polyethylenes, polypropylenes, polytetrafluoroethylenes, poly(tetrafluoroethylene-co-hexafluoropropenes), modified ethylene-tetrafluoroethylene copolymers, ethylene chlorotrifluoroethylene copolymers, polyvinylidene fluorides, polyethylene oxides, polyethylene terephthalates, silicones, polyurethanes, polyether block amides, and polyether esters. Suitable materials also include plastic, such as but not limited to polymethylmethacrylate (PMMA), polycarbonate, polytetrafluoroethylene (TEFLON), polyvinylchloride (PVC), polydimethylsiloxane (PDMS), polysulfone, polystyrene, polymethylpentene, polypropylene, polyethylene, polyvinylidine fluoride, ABS (acrylonitrile-butadiene styrene copolymer), and the like. In a specific example, the substrate can be glass. In another illustrative embodiment, the substrate can be polydimethylsiloxane (PDMS).

The microfluidic devices may be made according to any suitable process. For example, portions of a body of material may be removed to form a plurality of wall members from the channels. In these embodiments, the wall members may be integrally formed with the substrate. Examples of suitable material removal processes include, but are not limited to, bulk micromachining, sacrificial micromachining, focused ion-beam milling, electrostatic discharge machining, ultrasonic drilling, laser ablation, mechanical milling and thermal molding techniques. Conventional photolithographic and etching processes may be used to etch a body to form a plurality of wall members and fluid channels in the body. Etching processes such as, for example, reactive ion etching (RIE) or deep reactive ion etching (DRIE), or wet etching may be used to etch an appropriate body of material. In some embodiments, the wall members and the underlying substrate may be formed by molding. In other embodiments, wall members may be formed on a substrate. Wall members may also be formed on or bonded to a body to form a plurality of fluid channels. For example, wall members may be formed by electroplating (e.g., high aspect ratio plating). If desired, after the fluid channels are formed in the microdevice, the surfaces defining the fluid channels may be coated with a material such as but not limited to an adhesion layer, coupling agents, or substances that may potentially interact with fluids flowing through the fluid channels. Polymeric devices are readily manufactured using available microfabrication techniques, or from microfabricated masters, using molding techniques, such as injection molding, embossing or stamping, or by polymerizing the polymeric precursor material within the mold.

The channel portions of the devices typically include, at least in part, channel surfaces that have charged functional groups associated therewith, in order to produce sufficient EOF. A variety of methods may be used to provide substrate materials having an appropriate surface charge, including, but not limited to adsorptive modification through Van der Waals force, hydrogen bonding or electrostatic interaction; direct covalent modification through a silane bond; or indirect covalent modification through a silane or polymer linker.

In the case of silica-based substrates, negatively charged hydroxyl groups present upon the etched surfaces of the channels are typically sufficient to generate sufficient EOF upon application of a voltage gradient along such channels. An array of silicon-based molecules appropriate for functionalizing surfaces are commercially available. Appropriate molecules can be purchased commercially, synthesized de novo, or it can be formed by modifying an available molecule to produce one having the desired structure and/or characteristics. By way of example, the reactive groups on a number of siloxane functionalizing reagents can be converted to other useful functional groups, including, but not limited to, Hydroxyalkyl siloxanes, Diol (dihydroxyalkyl) siloxanes, Aminoalkyl siloxanes, and Dimeric secondary aminoalkyl siloxanes.

For substrates constructed of a plastic such as polypropylene, the surface can derivatized by chromic acid oxidation, and subsequently converted to hydroxylated or aminomethylated surfaces. Additionally, substrates made from highly crosslinked divinylbenzene can be surface derivatized by chloromethylation and subsequent functional group manipulation. The components of the disclosed device are typically compatible with the particular lipids, amphiphiles, analytes, and reagents with which the device is to be used and come in contact with. The device can contain amphiphilic membranes and be used to assay biological of chemical substances; hence, the device should not react with, degrade, or have any deleterious impact on the particular compounds that are to be analyzed. In a further aspect, the device should be stable towards and resist degradation from typical solvents used in biological or chemical applications and preparations.

In an illustrative embodiment, the channels and/or chambers of the microfluidic devices are typically fabricated into the upper surface of the bottom substrate or portion, as microscale grooves or indentations, using microfabrication techniques. The top portion or substrate also includes a first planar surface, and a second surface opposite the first planar surface. In some embodiments, the top portion also includes a plurality of apertures, holes or ports, e.g., from the first planar surface to the second surface opposite the first planar surface. The first planar surface of the top substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. The holes in the top portion of the device are oriented such that they are in communication with at least one of the channels and/or chambers formed in the interior portion of the device from the grooves or indentations in the bottom substrate. In the completed device, these holes function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device.

Amphiphilic Layers

In some embodiments, the interior of the channel of the microfluidic device is at least partially or completely coated by one or more amphiphilic layers, such as a lipid layer. The term "at least partially coated" means that a coating material is on the surface but it need not completely cover the surface. For example, a coating material can cover about 10% of a surface or more, discontinuously or continuously, or up to about 98% or about 100% of the surface. In some embodiments, the coating covers from about 20% to about 90% of the surface. The surface may be at least partially coated with one or more amphiphilic layers prior to or during EOF. In one embodiment, the amphiphilic molecules are added to the channels in the microfluidic device prior to initiating an EOF. In another embodiment, the amphiphilic molecules are added to a reservoir in fluid communication with the channel, such that when an EOF is applied and fluid in drawn through the channel, amphiphilic molecules in the reservoir replenish the layers that had formed in the device.

In general, any lipid capable of self-assembly can be used to produce the one or more amphiphilic layers. The lipid can have a tail of about four carbons to about 24 carbons or more. In some embodiments, the lipid has a tail of about 12 carbons to about 18 carbons. The lipid used to produce one or more amphiphilic layers can be a mixture of such lipids, and the different lipids can have tails of approximately the same length, of different lengths, i.e., lipids having different tail lengths can be combined.

The lipid can be any amphiphilic molecule, which is a molecule that possesses both hydrophilic and lipophilic properties. The lipid can be, but is not limited to, a phosphatidyl choline, a phosphatidyl ethanolamine, a phosphatidyl glycerol, a phosphatidyl serine, a phosphatidyl inositol, or a sphingomyelin, or a mixture of one or more of any of the above.

The lipid can be a mixture of different membrane lipids, e.g., a mixture of phosphatidyl choline and phosphatidyl ethanolamine.

In one embodiment, the amphiphilic layers disclosed herein can include an anionic lipid. Any anionic lipid can be used. Suitable anionic lipids are commonly used in detergents, shampoos, soaps, etc., and can be obtained commercially or prepared by methods known in the art. They include, and are not limited to, alkylbenzene sulfonates (detergent), fatty acid based surfactants, lauryl sulfate (e.g., a foaming agent), di-alkyl sulfosuccinate (e.g., a wetting agent), lignosulfonates (e.g., a dispersant), and the like, including mixtures thereof. In other non-limiting examples, linear alkylbenzene sulphonic acid, sodium lauryl ether sulphate, alpha olefin sulphonates, phosphate esters, sodium sulphosuccinates, hydrotropes, and the like, including mixtures thereof, can be used.

In another embodiment, the amphiphilic layers disclosed herein can include a cationic lipid. Any cationic lipid can be used. Suitable cationic lipids include, and are not limited to, quaternary ammonium compounds (e.g., tetraalkyl ammonium salts, pyridinium salts, imidazolinium salts, and the like). Such cationic lipids can be obtained commercially or can be prepared by methods known in the art. In an illustrative embodiment, a cationic phospholipid, such as but not limited to a phosphatidyl choline or a phosphatidyl serine may first be adsorbed on the interior of the microfluidic device, wherein the cationic charge in the polar head of the amphiphile adsorbs to a negative surface charge of an article such as a silica or a silicate.

In another embodiment, the amphiphilic layers disclosed herein can include a nonionic lipid. Any nonionic lipid can be used. Suitable nonionic lipids do not ionize in aqueous solution, because their hydrophilic group is of a non-dissociable type, such as but not limited to alcohol, phenol, ether, ester, or amide. They can be classified as ethers (e.g., polyhydric alcohols such as glycerin, solbitole, sucrose, etc.), fatty acid esters (e.g., glycerin fatty acid ester, sobitan fatty acid ester, sucrose fatty acid ester, etc.), esters (e.g., compounds made by applying, for example, ethylene oxide to a material having hydroxyl radicals such as high alcohol, alkyl-phenol, and the like), ether/esters (e.g., compounds made by applying, for example, the ethylene oxide to the fatty acid or polyhydric alcohol fatty acid ester, having both ester bond and ether bond in the molecule), and other types (e.g., the fatty acid alkanolamide type or the alkylpolyglyceride type). Other suitable examples of nonionic lipids can include, and are not limited to, alcohol ethoxylates and alkyl phenol ethyoxylates, fatty amine oxides, alkanolamides, ethylene oxide/propylene oxide block copolymers, alkyl amine ethoxylates, tigercol lubricants, etc.

In another embodiment, the amphiphilic layers disclosed herein can include dipolar lipids. Any dipolar lipid can be used. Suitable dipolar lipids (called amphoteric or zwitterionic) exhibit both anionic and cationic dissociation. Examples of dipolar lipids include, and are not limited to, products like betaines or sulfobetaines and natural substances such as amino acids and phospholipids.

In another embodiment, the amphiphilic layers disclosed herein can include additional membrane forming amphiphilic molecules. Any amphiphilic molecule can be used, examples of which comprise multiblock copolymers. Suitable examples of block copolymers include, and are not limited to, products like poly(methyl oxazoline)-poly(dimethyl siloxane)-poly(methyl oxazoline), poly(ethylene glycol)-poly(dimethyl siloxane)-poly(ethylene glycol), poly(ethylene oxide)-polybutadiene, poly(ethylene oxide)-polystyrene, poly(acrylic acid)-polystyrene, polyisoprene-poly(2-cinnamoylethyl methacrylate), polystyrene-(isocyano-L-alanine-L-alanine), poly(ethylene oxide)-poly(ethylene ethylene), poly(acrylic acid)-poly(methyl methacrylate), poly (methacrylic acid)-poly(neopentyl methacrylate), poly(t-butylmethacrylate)-poly(ethylene oxide), poly(methyl methacrylate)-poly(N,N-dimethylacrylamide), poly(butylacrylate)-poly(acrylic acid), poly(butadiene)-poly(methacrylic acid), poly(butadiene)-poly(acrylic acid), poly(isoprene)-poly(ethylene oxide), poly(ethylene)-poly(ethylene oxide), poly(ethylene-co-butene)-poly(ethylene oxide), poly(ethylene oxide)-poly(acrylic acid), poly(ethylene oxide)-poly(eta-caprolactone), poly(ethylene oxide)-poly(methyl methacrylate), poly(ethylene oxide)-poly(2-hydroxyethyl methacrylate), poly(ethylene oxide)-poly(methacrylic acid), poly(ethylene oxide)-poly(2-methyl oxazoline), poly(ethylene oxide)-polypropylene oxide), poly(ethylene oxide)-poly(t-butyl acrylate), poly(ethylene oxide)-poly(tetrahydrofurfuryl methacrylate), poly(ethylene oxide)-poly(acrylic acid), poly(ethylene oxide)-poly(methyl acrylate), poly(ethylene oxide)-poly(t-butyl methacrylate), poly(ethylene oxide)-poly(2-ethyl oxazoline), poly(isobutylene)-poly(ethylene oxide), polystyrene-poly(acrylic acid), polystyrene-polyacrylamide, poly(p-chloromethyl styrene)-polyacrylamide, poly(styrene-co-p-chloromethyl styrene)-poly(acrylic acid), polystyrene-poly(methacrylic acid), polysytrene-poly(N,N-dimethylacrylamide), poly(dimethylsiloxane)-poly(acrylic acid), poly(dimethylsiloxane)-poly(ethylene oxide), poly(2-vinyl naphthalene)-poly(acrylic acid), poly(2-vinyl pyridine)-poly(ethylene oxide), poly(N-methyl 2-vinyl pyridine)-poly(ethylene oxide), poly(vinyl pyrrolidone)-(D/L-lactide), poly(dimethylsiloxane)-block-poly(2-methyloxazoline) (PMOXA-PDMS-PMOXA), poly(ethylene oxide)-polypropylene oxide) (EO-PO-EO) poly(acrylic acid)-poly(9,9-di-n-hexyl-2,70-fluorene)-poly(acrylic acid), poly(n-butyl acrylate)-poly(9,9-di-n-hexyl-2,70-fluorene)-poly(n-butyl acrylate), poly(t-butyl acrylate)-poly(9,9-di-n-hexyl-2,70-fluorene)-poly(t-butyl acrylate), poly(t or n-butyl acrylate)-poly(methyl methacrylate)-poly(t or n-butyl acrylate), poly(t-butyl acrylate)-polystyrene-poly(t-butyl acrylate), poly(ethylene oxide)-poly(dimethylsiloxane)-poly(ethylene oxide), poly(ethylene oxide)-polystyrene-poly(ethylene oxide); poly(ethylene oxide)-poly(methylphenylsilane) pentablock: (PMPS-PEO)2-PMS.

Figure 2:
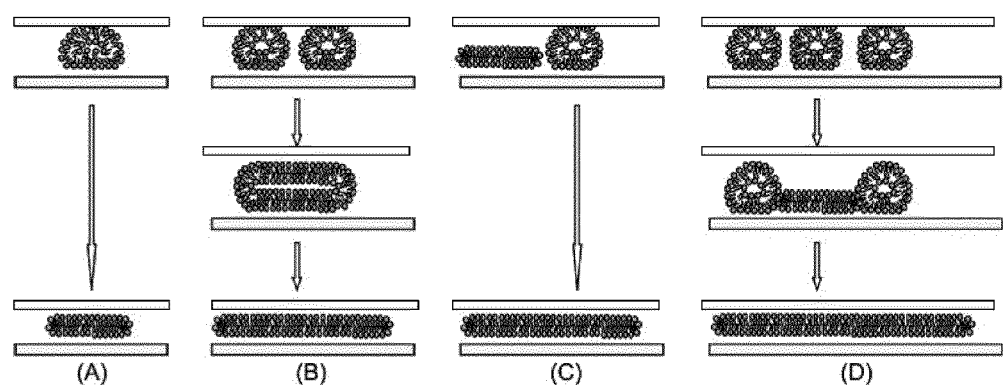
FIG. 2 is schematic illustration of the formation of amphiphilic layers in a microfluidic channel by vesicle rupture.

The interior of the channel can be at least partially covered with an amphiphilic layer in a variety of ways. In one embodiment, the amphiphilic layer is formed in the interior channel of the device by adding lipid-containing vesicles to the channel and rupturing the vesicles. Once a vesicle has ruptured, the resulting bilayer patch exposes an edge. These edges are energetically unfavorable and, at least from a thermodynamic perspective, expected to promote the interaction with adjacent lipid material, such as the rupture of surface-bound vesicles or vesicles from solution. Provided the density of adsorbed vesicles is sufficiently high, such a process can propagate in a cascade of rupture events across several neighboring vesicles and leads to the formation of extended bilayer patches. FIG. 2 is a schematic diagram illustrating how vesicle rupture may be used to form a lipid layer inside a channel FIG. 2A shows an isolated adsorbed vesicle ruptures spontaneously, driven by its support-induced deformation. FIG. 2B shows how neighboring adsorbed vesicles may fuse and eventually rupture. FIG. 2C shows how the active edge of a supported bilayer patch may induce the rupture of a neighboring vesicle. FIG. 2D shows how the cooperative action of several neighboring vesicles may lead to the rupture of a first vesicle (at the critical vesicular coverage). The active edge thereby exposed may trigger the rupture of adjacent vesicles. See, e.g., Langmuir, Vol. 22, No. 8, 2006 3499.

In another embodiment of a method for forming the amphiphilic layers in the interior channel of the device, a lipid bilayer is formed on a solid support and then transferred into the tube or channel. In one embodiment, supported lipid bilayers are formed by self-assembly. Both lecithins and cetyl trimethyl ammonium bromide (CTAB) can adsorb from aqueous solution to form "self-assembled" bilayers on mica (surface area of mica used 1-2 $cm^2$). CTAB is easily adsorbed from solution because of its high critical micelle concentration of 0.8 mM. (Helm, C., Israelachvili, J., McGuiggan, P., Role of Hydrophobic Forces in Bilayer Adhesion and Fusion, Biochemistry, 1992, 31, 1794-1805, Israelachvili, J. N., Pashley, R. M. (1982) J. Colloid Interface Sci. 98, 500.) Other lecithin bilayers can be formed by deposition onto quartz and evaporation of chloroform. (Starr, T., Thompson, N., Formation and Characterization of Planar Phospholipid Bilayers supported on $TiO_2$ and $SrTiO_3$ Single Crystals, Langmuir 2000, 16, 10301-10308.)

Figure 3:
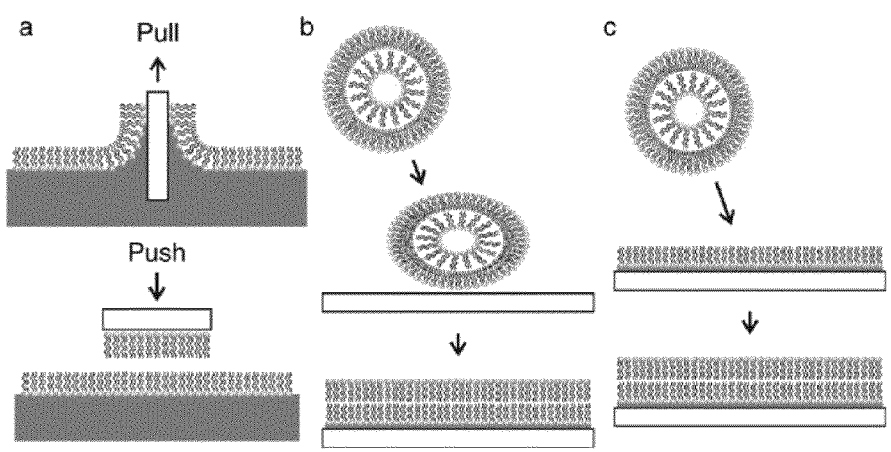
FIG. 3 is a schematic illustration of techniques for the formation of supported lipid bilayers.

In another embodiment, supported phospholipid bilayers may be formed on planar supports by Langmuir-Blodgett techniques and vesicle fusion. The first method involves the transfer of a lower leaflet of lipids from the air-water interface by the Langmuir-Blodgett technique (FIG. 3a). This is followed by the transfer of an upper leaflet by the Langmuir-Schaefer procedure, which involves horizontally dipping the substrate to create the second layer. A second method of supported bilayer formation is the adsorption and fusion of vesicles from an aqueous suspension to the substrate surface (FIG. 3b). Also, a combination of the two methods can be employed by first transferring a monolayer via the Langmuir-Blodgett technique followed by vesicle fusion to form the upper layer (FIG. 3c). Castellana, E., Cremer, P., Solid supported lipid bilayers: From biophysical studies to sensor design, Surface Science Reports, 61 (2006)429-444.

Figure 4:
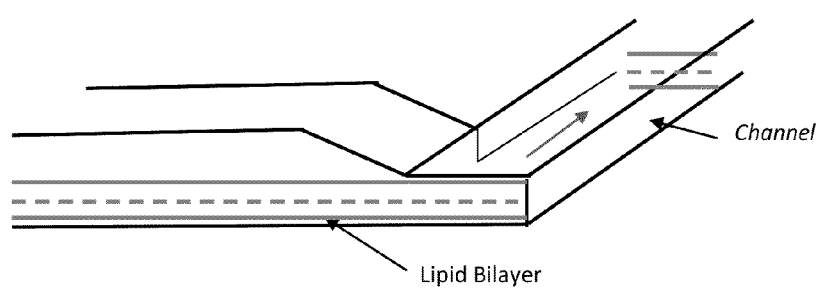
FIG. 4 is an illustrative embodiment showing the shape change that could be used to form a lipid bilayer and then transfer the bilayer into a channel. Transfer would be accomplished by separation of a stressed lipid bilayer.

In one embodiment, once the solid-supported lipid bilayer is formed, the lipid bilayer is moved into a channel of a microfluidic device. One way to move a lipid bilayer into a channel is by forming a supported bilayer (by self-assembly or other method discussed above), then moving it into a channel through shape change. A variety of shape changes may be used, although one illustrative embodiment is shown in FIG. 4. Movement into the channel may be passive which could be accomplished by forming a gradient in surface energy on the surface, or movement may be active by EOF. Once the lipid bilayer moves into the channel, active movement by EOF may predominate. The lipid bilayer may separate allowing a section to move through the channel.

Figure 5:
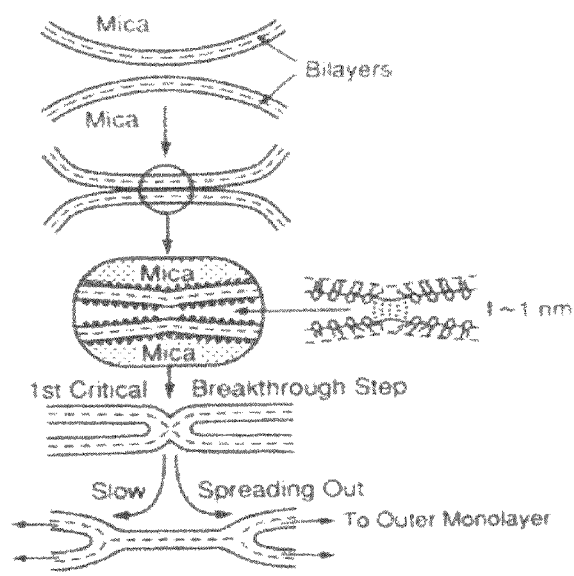
FIG. 5 is an illustrative embodiment showing the hemifusion of two adsorbed (supported) bilayers on mica in aqueous solutions. The critical breakthrough Step C is followed by sliding out of the lipids from the fused outer monolayers until a single hemifused bilayer remains at Step E.
Figure 6:
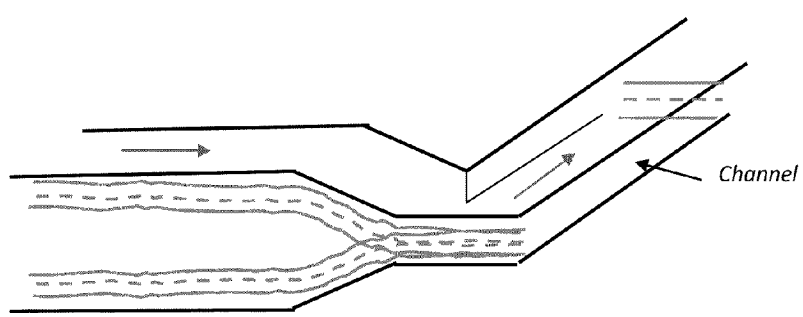
FIG. 6 is an illustrative embodiment of how two lipid bilayers would be fused into a channel. Fusion would take place by the mechanism as shown in FIG. 5. A greater number of lipid bilayer defects facilitates fusion of two bilayers.

In another embodiment, a lipid bilayer may be formed in a channel by forming two supported bilayers, and then joining them together through fusion (FIG. 5). (Helm, C., Israelachvili, J., McGuiggan, P., Role of Hydrophobic Forces in Bilayer Adhesion and Fusion, Biochemistry 1992, 31, 1794-1805). For instance, channel wall materials may be a mica-like material for the top and bottom, and silicon nitride for the channel sides (the same material used in forming bilayers in apertures, where the silicon nitride makes contact with the bilayer edges (FIG. 6).

In one embodiment, the one or more amphiphilic layers form wormlike micelles. Wormlike micelles are elongated flexible self-assembly structures formed by the aggregation of amphiphiles. Above a threshold concentration, they entangle into a dynamic network, reminiscent of polymer solutions, and display remarkable visco-elastic properties, which have been exploited in numerous industrial and technological fields. The most well-known and studied wormlike micelles systems are cationic surfactants with a long aliphatic chain, such as cetyl trimethylammonium bromide (CTAB) or cetylpyridinium bromide (CPBr), for which micellar growth takes place at relatively high concentration or in the presence of salt. In addition to those systems, numerous surfactants have been found to form wormlike micelles, in the presence of cosurfactants, additives, salts or appropriate counter-ions. The overall length of the micelles is referred to as the contour length L and varies between a few nanometers to micrometers. Wormlike micelles can be extremely flexible and micrometers long. One of the most widely studied lipid-based surfactant forming wormlike micelles is lecithin (or phosphatidylcholine), a major component of the lipid matrix of biological membranes, also used in pharmaceutical formulations as it is well-tolerated and non-toxic. Lecithin forms giant reverse micelles in organic solvents (cyclohexane, isooctane, decane) and micellar growth is usually promoted by addition of small amounts of water.

Non-polar solvents may be introduced into the lipid bilayer. In one embodiment, a non-polar solvent (e.g., hexane) is introduced to a bilayer by control of vapor phase (via hexane/hexadecane mixtures). The hexane enters the bilayer in the vapor phase and is shown to be confined to the center of the bilayer. The amount of hexane in the interior of the membrane depends on the hexane vapor pressure. The intercalation of nonpolar solvents can be assisted by maximizing defects in the lipid bilayer. Nonpolar solvents may also be introduced into the lipid bilayer by a variety of methods such as but not limited to adsorption of a small n-alkane between a planar phospholipid bilayer. See for example, White, S. H., King, G. I., Cain, J. E., *Location of Hexane in Lipid Bilayers determined by Neutron Diffraction*, Nature Vol. 290, 1981, p. 161; Smith, R. A., Porter, R. G., and Miller, K. W., *The Solubility of Anesthetic Gases in Lipid Bilayers*, Biochimica et Biophysica Act, 645, (1981) p. 327-338; Gruen, D., Haydon, D., *The Adsorption of Nonpolar Molecules into Lipid Bilayer Membranes*, Biophys., J., Vol. 30, 1980, p. 129-136; Pope, J. M., Dubro, D. W., *The interaction of n-alkanes and n-alcohols with lipid bilayer membranes: a 2H-NMR study*, Biochemica et Biophysica Acta 858 (1986) 243-253.

Any suitable nonpolar solvent can be used in the device. Examples of suitable nonpolar solvents include, and are not limited to, propane, butane, pentane, hexane, heptane, octane, nonane, decane, hexadecane, cyclopentane, cyclohexane, benzene, toluene, squalene, xylene, diethyl ether, diisopropylether, ethylacetate, 2-butanone, carbon tetrachloride, chloroform, methylene chloride, tetrachloroethane, trichlorethane, dichloroethane, ethyl acetate, and the like. In one particular example, the organic solution includes 1:1 squalene:N-decane. The organic solution can contain buffers, preservatives, surfactants, stabilizers, proteins or other biomolecules of interest, and the like.

Other components of cell membranes can also be included in the membrane lipid, thereby producing membranes containing incorporated cell membrane components, e.g., receptor proteins, transport proteins, ion channel proteins, antibody receptor proteins, signaling proteins, etc. Such components may be useful for conducting biological assays in the microfluidic device. For instance, membrane-bound proteins are important from both a scientific and a technological point of view. However, their study and application require a stable lipid bilayer to maintain protein function. In some embodiments, the present devices can provide lipid bilayers which allow for insertion of transmembrane proteins, such as the staphylococcal protein pore agr-hemolysin. In one embodiment, the presence of a protein in the membrane could 'stress' the membrane, making it easier to deform the bilayer in the channel, to cleave the bilayer apart, or to fuse with other lipid bilayer membranes in intersecting channels. In another embodiment, a membrane protein may participate in chemical reactions, i.e., add a functional group to a nonpolar agent prior to it gaining entry to the lipid bilayer.

Methods of Using the Microfluidic Devices

In one aspect, the movement of nonpolar solutions through microfluidic channels occurs when a hydrophilic, charged headgroup of the one or more lipid layers and the associated counter ions interact with the microchannel wall. In an aqueous system, the polar heads of lipids align towards the polar, aqueous environment, while the hydrophobic tails minimize their contact with water and tend to cluster together. During the course of EOF, the lipid layer moves through the channel, dragging with it the non-polar solvent or reaction mixtures that are contained within the lipid interior. The movement of the nonpolar solutions through the microfluidic channels can be controlled in any manner known to one of ordinary skill in the art. For example and without limitation, the solutions can be moved through the microfluidic channels with syringe pumps, external and internal peristaltic pumps, by applying a vacuum, by applying an electric potential, by allowing a gas to flow over and/or through the microfluidic channels. Also, temperature gradients can move volumes of solutions through the microfluidic channels.

In some embodiments, EOF is used to move nonpolar solvents through the microfluidic devices. In order to generate the EOF, an electric field is deployed at the ends of the microfluidic channel. Typically, this field can run from about 100 v/cm to 1000 v/cm. The field determines the EOF velocity. Weaker fields can be used, but the flow will proceed more slowly. Stronger fields can be used provided that they do not result in electrolysis of the solvent. This field can be established using thin film electrodes of a type known in the art. An electrode is typically selected which does not result in the formation of precipitates and which does not produce appreciable gas through electrolysis. Silver or platinum electrodes are well known and can be used, but other electrodes having a higher overpotential which can be deposited by sputtering may prove to be more desirable for use.

Valves can also be used in fluid flow control. Valves can be actuated by applying an external force, such as a blade, cantilever, or plug to a channel. Channels also can contain membranes that can be deflected by air pressure and/or liquid pressure, e.g., water pressure, electrostatically, or magnetically. One-way or "check valves" also can be formed in microchannels with balls, flaps, or diaphragms.

Microscale mixing and separation components are useful to facilitate reactions and evaluate products. In microfluidic devices, mixing is most often done by diffusion, in channels of long length scales, curved, with variable widths, or having features that cause turbulence. Mixing also can be accomplished electroosmotically or ultrasonically. The walls of microfluidic chambers also can be functionalized with a variety of ligands that can interact or bind to an analyte or to a contaminant in an analyte solution. Such ligands include, but are not limited to, hydrophilic or hydrophobic small molecules, steroids, hormones, fatty acids, polymers, RNA, DNA, PNA, aptamers, amino acids, peptides, proteins (including antibody binding proteins such as protein G), antibodies or antibody fragments (FABs, etc.), antigens, enzymes, carbohydrates (including glycoproteins or glycolipids), lectins, cell surface receptors (or portions thereof), species containing a positive or a negative charge, and the like.

As noted above, the channel portions are typically fabricated into a planar solid substrate. Electrodes are disposed in electrical contact with the ends of the channel. These electrodes are in turn, coupled to power source, which delivers appropriate voltages to the electrodes to produce the requisite voltage gradient. Application of a voltage gradient between the cathode and anode, results in the propagation of EOF within the channel. The direction of fluid flow depends upon the direction of the voltage gradient applied as well as the nature of the surface charge. Differential surface charges, whether oppositely charged, or having varied charge densities among two or more channels, may be achieved by well known methods. For example, surfaces are optionally treated with appropriate coatings, e.g., neutral or charged coatings, charge neutralizing or charge adding reagents, e.g., protecting or capping groups, silanization reagents, and the like, to enhance charge densities, and/or to provide net opposite surface charges, e.g., using aminopropylsilanes, hydroxypropylsilanes, and the like.

Applications of the Microfluidic Devices

Various microfluidic devices can be used to perform analyses on a microfluidic scale. The microdevice may include a plurality of fluid channels defined by a plurality of wall members. The plurality of wall members may include at least one wall member having at least one opening that communicates two adjacent fluid channels. Different chemical reactants may be added to the different channels and then mixed in the device.

In some embodiments, the device can be used to rapidly detect characteristics of a plurality of different fluids. Fluids include organic fluids, solvents, and the like. Regardless of the form of the fluids, the fluids may include organic or inorganic molecules. In some embodiments, the different fluids flow through a plurality of different fluid channels at a detection region of a microdevice. The different fluids may have distinct characteristics and may be the products of events that occur before the different fluids flow through the detection region of the microdevice. For example, the different fluids may be downstream products of upstream events such as potential or actual interactions between substances. Events may include chemical or biological reactions between two substances or binding events between two substances.

The characteristics of the fluids that are detectable may be either quantitative or qualitative in nature. In some embodiments, characteristics of the fluids such as but not limited to emitted radiation (e.g., light), conductivity, pH, etc. of the different fluids flowing in the different fluid channels can be detected to analyze and/or characterize the different fluids. Such characteristics may correspond to the types and/or amount of substances in the fluids. In some embodiments, the detected characteristics may serve as a direct or an indirect indicator of the concentration or amount of a particular substance in the fluid. For example, solutions containing protons are conductive. The conductivity or resistance of a fluid may be an indirect indicator of the concentration of protons in the fluid.

Chemical interactions that can be assayed using the microfluidic device may be any type of interaction normally observed for biological or chemical moieties including, for example, a catalytic reaction of an enzyme or a binding event. In some embodiments, separate fluid samples can be screened for their ability to interact with a biological or chemical moiety. For example, different fluid samples containing respectively different substances can flow through separate fluid channels in a microdevice and can be delivered to separate reaction sites on the microdevice. Each of the reaction sites may include an immobilized moiety, and the immobilized moieties may be bound to respective surfaces of different fluid channels. At the reaction sites, the moieties may or may not interact with the different fluid samples. Downstream of the reaction sites, the characteristics of the different fluids may be detected, either directly or indirectly to determine if any of the fluids of the substances in the different fluids have interacted (e.g., by binding together) with the immobilized moiety at each reactive site. For example, one or more detection devices downstream of the reactive sites may measure the concentration of the different substances in the fluids passing downstream of the reaction sites by detecting characteristics of the fluids. If the concentration of a substance in a fluid passing downstream of a reaction site is less than the concentration of the substance in a fluid upstream of the reaction site, then it is likely that the substance in the fluid is interacting (e.g., binding or reacting) with the immobilized moiety. On the other hand, if the concentration of a substance in a fluid downstream of the reaction site is substantially equal to the concentration of the substance upstream of the reaction site, then it is likely that little or no interaction is occurring between the substance in the fluid and the immobilized moiety.

In another example, specific conditions may be applied to different fluids in the different fluid channels to see if the fluids or substances in the fluids change as a result of the conditions. For instance, a plurality of different fluids may be subjected to different heating, cooling, and irradiation (e.g., with light) conditions. Characteristics in the fluids passing downstream of these events may be detected to determine if the conditions affect the fluids.

In some embodiments, characteristics of the different fluids in the fluid channels may be detected by using a probe. The probe may pass through fluid channels by passing through openings in wall members that define the fluid channels. The characteristics of the fluids in these fluid channels can be quickly detected without exposing the end of the probe to an environment outside of the flowing fluid. Illustratively, a probe for a pH sensor may be placed in a fluid channel to detect the pH of the fluid in that channel. Once the probe is in contact with the fluid in the channel, the pH of the fluid in the channel can be detected.

The detection methods, detection assemblies, and analytical systems are not limited to those described above, and may employ any suitable optical, electrical, physical, and/or chemical detection techniques. Radiation such as visible, infrared, or ultraviolet radiation from the fluids may be detected by a detection assembly being an optical detection assembly. The probe may comprise a physical sensor, a biological sensor, a chemical sensor, or an electrical sensor. Examples of physical sensors include thermocouples, pressure sensors, flow sensors, optical fibers, etc. Examples of biological sensors include sensors with immobilized enzymes or immunoassays. Examples of electrical or chemical sensors include sensors with interdigitated electrodes having optional polymer coatings, atomic force microscopes (AFMs), Ion Sensitive Field Effect Transistors (ISFETs), light addressable potentiometric sensors (LAPSs), pH meters, and scanning probe potentiometers (SPPs). In comparison to optical detection devices, chemical sensors and electrical sensors are desirable as they do not need to use more expensive and inconvenient fluorescent or radiochemical tagging processes.

In some embodiments, the microfluidic devices may be used in a variety of applications, including, e.g., the performance of high throughput screening assays in drug discovery, immunoassays, diagnostics, genetic analysis, and the like. As such, the devices described herein will often include multiple sample introduction ports or reservoirs, for the parallel or serial introduction and analysis of multiple samples. Alternatively, these devices may be coupled to a sample introduction port, e.g., a pipettor, which serially introduces multiple samples into the device for analysis.

In other embodiments, the microfluidic devices are useful for interfacing with more conventional systems, e.g., conventional analytical equipment, such as mass spectrometers, HPLC, GC, etc. Specifically, these devices are capable of injecting small amounts of fluid from a microfluidic system into a fluid interface to such equipment without requiring a potential gradient through that interface.

EXAMPLES

The present disclosure is further illustrated by the following examples, which should not be construed as limiting in any way.

Example 1

Fabrication of Microfluidic Devices Containing a Lipid Bilayer

This example describes the fabrication of a microfluidic device containing an lipid bilayer. The device consists of a channel etched through a silicon wafer. The silicon devices are fabricated from double-polished, silicon nitride coated, n-type Si(100) wafers. The fabrication process is as follows: an aperture is first defined in the silicon nitride film on the backside of the wafer by photolithography and reactive-ion etching, using a C2F6 plasma (100 W, 15 mT and 20 ml min-1 C2F6) and a photoresist etch mask. The upper area of the well is then similarly defined on the front-side of the wafer. To etch through the bulk silicon and create the suspended silicon nitride membrane, the wafer is immersed in a 4.5M KOH solution at a temperature of 80° C. for approximately 8 hours. After dicing the wafer into individual devices, the exposed regions of silicon are then electrically insulated by coating the devices on both sides with 100 nm PECVD silicon nitride. A Pt electrode is formed on each surface of the well by a sputtering method. A Pt wire having a diameter of 0.1 mm is formed on each surface to form an electroosmotic flow pump.

Using adhesive, the silicon device was first bonded over a fluidic channel etched in a glass substrate and a glass well is then bonded over the upper surface of the silicon chip to create the upper and lower fluidic reservoirs. To form a lipid layer in the channel, the channel is first filled with electrolyte solution (1M KCl). 1-2 μl of 1 mg ml$^{-1}$ 1,2-diphytanoyl-sn-glycero-3-phosphocholine, diluted with n-decane, is then added to the channel to form the amphiphilic layer. A suitable non-polar solvent is added, which would localize between to amphiliplic layers, i.e. at the interior of the channel.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 units refers to groups having 1, 2, or 3 units. Similarly, a group having 1-5 units refers to groups having 1, 2, 3, 4, or 5 units, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

What is claimed is:

1. A microfluidic device comprising: at least one fluid channel and at least one pair of electrodes configured to provide an electric field in the at least one channel, wherein the interior of the at least one channel is at least partially coated by an amphiphile forming a lipid bilayer, the lipid bilayer comprising an intercalated non-polar solvent and the interior of at least one channel comprises two or more materials selected from the group consisting of: mica, glass, quartz, platinum, stainless steel, copper, aluminum, nickel, gold, titanium, ceramic, diamond, silicon, silicon nitride, silicone, high-density polyethylene, polyethylene terephthalate, polydimethylsiloxane, polymethyl-methacrylate, polystyrene, cellulose acetate, polyimide, and polycarbonate.

2. The device of claim 1, wherein the lipid bilayer comprises a phospholipid, sphingolipid, or glycolipid.

3. The device of claim 2, wherein the phospholipid is selected from the group consisting of: phosphatidylcholine, phosphatidylserine, phosphatidylethanolamine, and phosphatidylglycerol.

4. The device of claim 1, wherein the lipid bilayer has a fatty acyl chain length which defines a volume of an interior hydrophobic region of the channel.

5. The device of claim 4, wherein the fatty acyl chain length is about 2 carbons to about 24 carbons.

6. The device of claim 1, wherein the interior of the at least one channel is completely covered by the lipid bilayer.

7. The device of claim 1, wherein the at least one channel has a diameter of about 0.1 μM to about 500 μm.

8. The device of claim 1 further comprising a voltage controller in electrical contact with the at least one pair of electrodes.

9. The device of claim 1 further comprising one or more input ports and one or more output ports in fluid communication with the at least one channel.

10. A method of circulating or conducting a non-polar fluid, the method comprising:
adding a non-polar fluid to a microfluidic device comprising at least one fluid channel and at least one pair of electrodes configured to provide an electric field in the at least one channel, wherein the interior of the at least one channel is at least partially coated by an amphiphile forming a lipid bilayer, the lipid bilayer comprising an intercalated non-polar solvent and the interior of at least one channel comprises two or more materials selected from the group consisting of: mica, glass, quartz, platinum, stainless steel, copper, aluminum, nickel, gold, titanium, ceramic, diamond, silicon, silicon nitride, silicone, high-density polyethylene, polyethylene terephthalate, polydimethylsiloxane, polymethyl-methacrylate, polystyrene, cellulose acetate, polyimide, and polycarbonate; and
applying an electric field to the at least one fluid channel to generate an electro-osmotic flow.

11. The method of claim 10, wherein the non-polar fluid is selected from the group consisting of: propane, butane, pentane, hexane, heptane, octane, nonane, decane, cyclopentane, cyclohexane, benzene, toluene, xylene, squalene, diethyl ether, diisopropylether, ethylacetate, 2-butanone, carbon tetrachloride, chloroform, methylene chloride, tetrachloroethane, trichlorethane, dichloroethane, and ethyl acetate.

12. The method of claim 11, wherein the lipid bilayer forms a hydrophobic space in the interior of the channel.

13. The method of claim 11, wherein the lipid bilayer comprises a phospholipid, sphingolipid, or glycolipid.

14. The method of claim 13, wherein the phospholipid is selected from the group consisting of: phosphatidylcholine, phosphatidylserine, phosphatidylethanolamine, and phosphatidylglycerol.

15. The method of claim 11, wherein the one or more lipid layers has a fatty acyl chain length of about 2 carbons to about 24 carbons which defines the volume of an interior hydrophobic region of the channel.

* * * * *

UNITED STATES PATENT AND TRADEMARK OFFICE
CERTIFICATE OF CORRECTION

Page 1 of 1

PATENT NO. : 8,821,702 B2
APPLICATION NO. : 13/382498
DATED : September 2, 2014
INVENTOR(S) : Sjong It is certified that error appears in the above-identified patent and that said Letters Patent is hereby corrected as shown below:

In the Specification

In Column 1, Lines 8-9, delete "national stage application of International Application" and insert -- national stage filing under 35 U.S.C. §371 of International Application --, therefor.

In Column 3, Line 25, delete "is schematic" and insert -- is a schematic --, therefor.

In Column 3, Line 28, delete "is schematic" and insert -- is a schematic --, therefor.

In Column 4, Line 62, delete "mateiral" and insert -- material --, therefor.

In Column 9, Line 60, delete "channel FIG.2A" and insert -- channel. FIG.2A --, therefor.

In Column 9, Line 17, delete "-polypropylene oxide)," and insert -- -poly(propylene oxide), --, therefor.

In the Claims

In Column 16, Line 67, in Claim 7, delete "0.1µM" and insert -- 0.1µm --, therefor.

Signed and Sealed this
Tenth Day of March, 2015

Michelle K. Lee
*Deputy Director of the United States Patent and Trademark Office*